(12) United States Patent
Kaneko

(10) Patent No.: US 11,925,506 B2
(45) Date of Patent: Mar. 12, 2024

(54) ULTRASONIC IMAGE DIAGNOSTIC APPARATUS, IDENTIFIER CHANGING METHOD, AND IDENTIFIER CHANGING PROGRAM

(71) Applicant: Konica Minolta, Inc., Tokyo (JP)

(72) Inventor: Shikou Kaneko, Niiza (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 17/731,349

(22) Filed: Apr. 28, 2022

(65) Prior Publication Data

US 2022/0354453 A1    Nov. 10, 2022

(30) Foreign Application Priority Data

May 6, 2021    (JP) .................................. 2021-078448

(51) Int. Cl.
*A61B 8/08* (2006.01)
*A61B 8/00* (2006.01)

(52) U.S. Cl.
CPC .............. *A61B 8/085* (2013.01); *A61B 8/463* (2013.01); *A61B 8/5223* (2013.01); *A61B 8/54* (2013.01); *A61B 8/5292* (2013.01)

(58) Field of Classification Search
CPC ....... A61B 8/085; A61B 8/463; A61B 8/5223; A61B 8/54; A61B 8/5292; A61B 8/4405
See application file for complete search history.

(56) References Cited

U.S. PATENT DOCUMENTS 9,589,374 B1 *   3/2017   Gao ..................... A61B 6/5211
2021/0045717 A1 * 2/2021   Schwab ................. A61B 5/11
2021/0077061 A1 * 3/2021   Pinkovich ............. G16H 30/40

FOREIGN PATENT DOCUMENTS

JP      2020-501289 A        1/2020
KR      20190113089 A    *  10/2019

* cited by examiner

*Primary Examiner* — Joseph M Santos Rodriguez
*Assistant Examiner* — Kaitlyn E Sebastian
(74) *Attorney, Agent, or Firm* — RANKIN, HILL & CLARK LLP

(57) ABSTRACT

An ultrasonic image diagnostic apparatus includes: an ultrasonic image acquisitor that acquires an ultrasonic image generated on the basis of a reception signal obtained by an ultrasonic probe that transmits and receives ultrasonic waves to and from a subject; an identification result acquisitor that acquires, by inputting the ultrasonic image acquired to any of a plurality of identifiers that identifies an identification target object captured in an input ultrasonic image, an identification result output from the identifier; and a hardware processor that changes the identifier to which the ultrasonic image acquired is input.

16 Claims, 3 Drawing Sheets

ULTRASONIC IMAGE DIAGNOSTIC APPARATUS, IDENTIFIER CHANGING METHOD, AND IDENTIFIER CHANGING PROGRAM

The entire disclosure of Japanese patent Application No. 2021-078448, filed on May 6, 2021, is incorporated herein by reference in its entirety.

BACKGROUND

Technological Field

The present invention relates to an ultrasonic image diagnostic apparatus, an identifier changing method, and an identifier changing program.

Description of the Related Art

Conventionally, them is known an ultrasonic image diagnostic apparatus that transmits and receives ultrasonic waves to and from a subject such as a living body by an ultrasonic probe, generates ultrasonic image data on the basis of a signal obtained from the received ultrasonic waves, and displays an ultrasonic image based on the ultrasonic image data on an image display device. The ultrasonic image diagnosis by the ultrasonic image diagnostic apparatus can obtain the state of heartbeats, movement of a fetus, or the like in real time by a simple operation of simply placing the ultrasonic probe onto a body surface of the subject, and can be repeatedly performed because it is non-invasive and highly safe.

Meanwhile, as an image recognition technology for identifying a subject or the like captured in an image, a technology using machine learning such as deep learning is known.

In this type of image recognition technology, machine learning using a teacher image is performed on an identifier (for example, convolutional neural network; hereinafter also referred to as "CNN") to grasp a characteristic of a potential probability distribution in image data. The identifier having undergone the learning typically becomes capable of identifying an image pattern only by inputting pixel value information of the image.

JP 2020-501289 A describes a technique for automatically detecting nerves in a series of echo images in order to assist work of an anesthesiologist in the field of analysis of digital images by ultrasonic scanning. In the technique described in JP 2020-501289 A, a nerve-like region is generated in an echo image with a probability distribution, and a nerve is classified with respect to a region determined by the generated probability distribution.

Meanwhile, them is a plurality of nerves (for example, median nerve, ulnar nerve, radial nerve, brachial plexus, and the like) having different image characteristics represented in an ultrasonic image. Further, even in the same nerve, the appearance of the image is completely different depending on the position where the ultrasonic probe is placed. In addition, there is a plurality of traveling arrangement patterns of the nerve itself and other than the nerve (blood vessels, fats, and muscles) depending on a person. Even for the same person, the traveling or arrangement pattern of the nerve itself and other than the nerve is different between the left side and the right side. As described above, for the nerve, there is a very large number of image patterns to be identified.

In order to improve identification accuracy of the identification target object having a quite large number of image patterns like the nerve described above, in a case where an identifier (CNN) is used as an image recognition technology for identifying the identification target object captured in the ultrasonic image, it is conceivable to use a plurality of identifiers optimized for each identification target object while switching the plurality of identifiers. However, in this case, a complicated user interface (UI) operation for switching a plurality of identifiers optimized for individual sites is required, and there is a problem that it is difficult for a user (for example, a doctor) to perform a treatment (for example, puncture) that the user originally desires.

SUMMARY

An object of the present invention is to provide an ultrasonic image diagnostic apparatus, an identifier changing method, and an identifier changing program capable of reducing time and labor for switching an identifier in a case of identifying an identification target object captured in an ultrasonic image using the identifier.

To achieve the abovementioned object, according to an aspect of the present invention, an ultrasonic image diagnostic apparatus reflecting one aspect of the present invention comprises: an ultrasonic image acquisitor that acquires an ultrasonic image generated on the basis of a reception signal obtained by an ultrasonic probe that transmits and receives ultrasonic waves to and from a subject; an identification result acquisitor that acquires, by inputting the ultrasonic image acquired to any of a plurality of identifiers that identifies an identification target object captured in an input ultrasonic image, an identification result output from the identifier; and a hardware processor that changes the identifier to which the ultrasonic image acquired is input.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
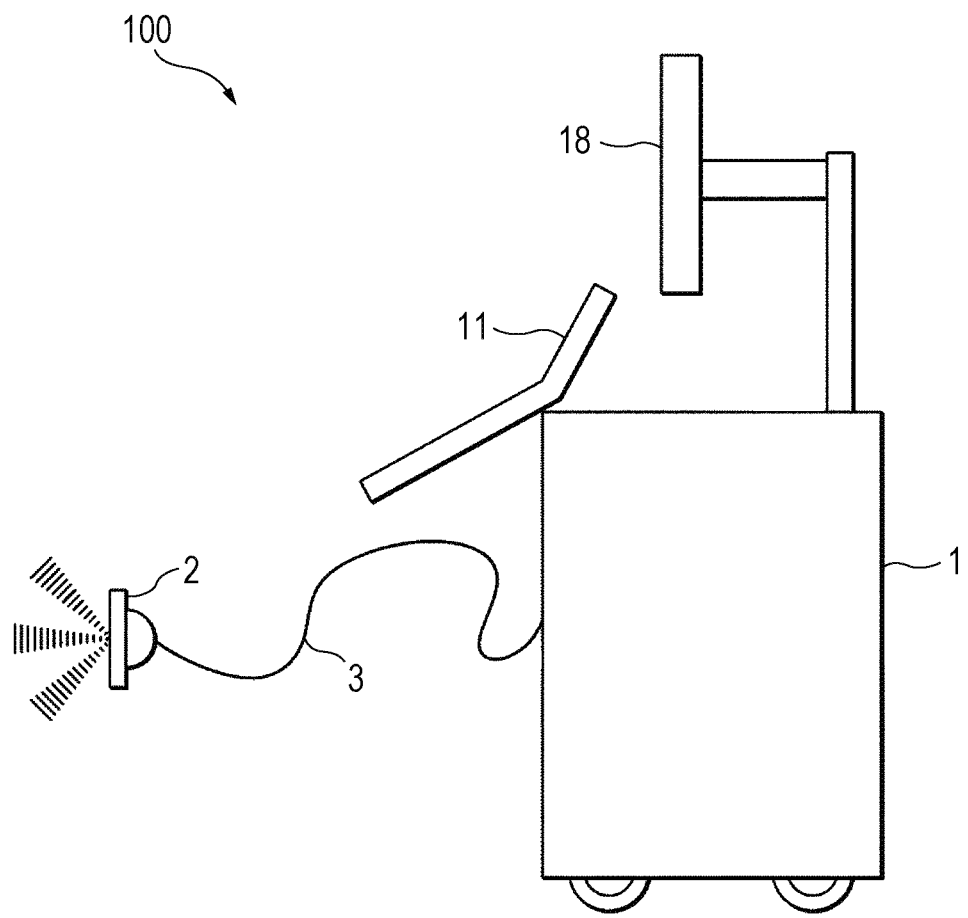
FIG. 1 is an external view of an ultrasonic image diagnostic apparatus.

Hereinafter, an ultrasonic image diagnostic apparatus 100 according to one or more embodiments of the present invention will be described with reference to the drawings. However, the scope of the invention is not limited to the disclosed embodiments. FIG. 1 is an external view of the ultrasonic image diagnostic apparatus 100.

As illustrated in FIG. 1, the ultrasonic image diagnostic apparatus 100 includes an ultrasonic image diagnostic apparatus main body 1 and an ultrasonic probe 2. Note that a mobile terminal such as a tablet terminal or a smartphone may be used as the ultrasonic image diagnostic apparatus main body 1.

The ultrasonic probe 2 transmits ultrasonic waves (transmission ultrasonic waves) to the inside of a subject such as a living body that is not illustrated, and receives reflected waves (reflected ultrasonic waves: echo) of the ultrasonic waves reflected in the subject.

The ultrasonic image diagnostic apparatus main body 1 is connected to the ultrasonic probe 2 via a cable 3, and causes the ultrasonic probe 2 to transmit transmission ultrasonic waves to the subject by transmitting a drive signal of an electric signal to the ultrasonic probe 2.

Further, the ultrasonic image diagnostic apparatus main body 1 images an internal state in the subject as an ultrasonic image on the basis of a reception signal that is an electric signal generated by the ultrasonic probe 2 in response to reflected ultrasonic waves from the inside of the subject received by the ultrasonic probe 2. Further, the ultrasonic image diagnostic apparatus main body 1 includes an operation input unit 11 and a display 18 described later.

The ultrasonic probe 2 includes an oscillator 2a (see FIG. 2) including a piezoelectric element, A plurality of oscillators 2a is arranged in a one-dimensional array in an orientation direction (scanning direction), for example. In the present embodiment, for example, an ultrasonic probe 2 having 192 oscillators 2a is used.

Note that the oscillators 2a may be arranged in a two-dimensional array. Further, the number of oscillators 2a can be arbitrarily set. Furthermore, in the present embodiment, a linear electron scan probe is used as the ultrasonic probe 2 to scan the ultrasonic waves by a linear scanning method, but any method of a sector scanning method, a convex scanning method, a radial scanning method, and a circular scanning method can be employed. The communication between the ultrasonic image diagnostic apparatus main body 1 and the ultrasonic probe 2 may be performed by wireless communication using Ultra Wide Band (UWB) or the like instead of the wired communication via the cable 3.

Figure 2:
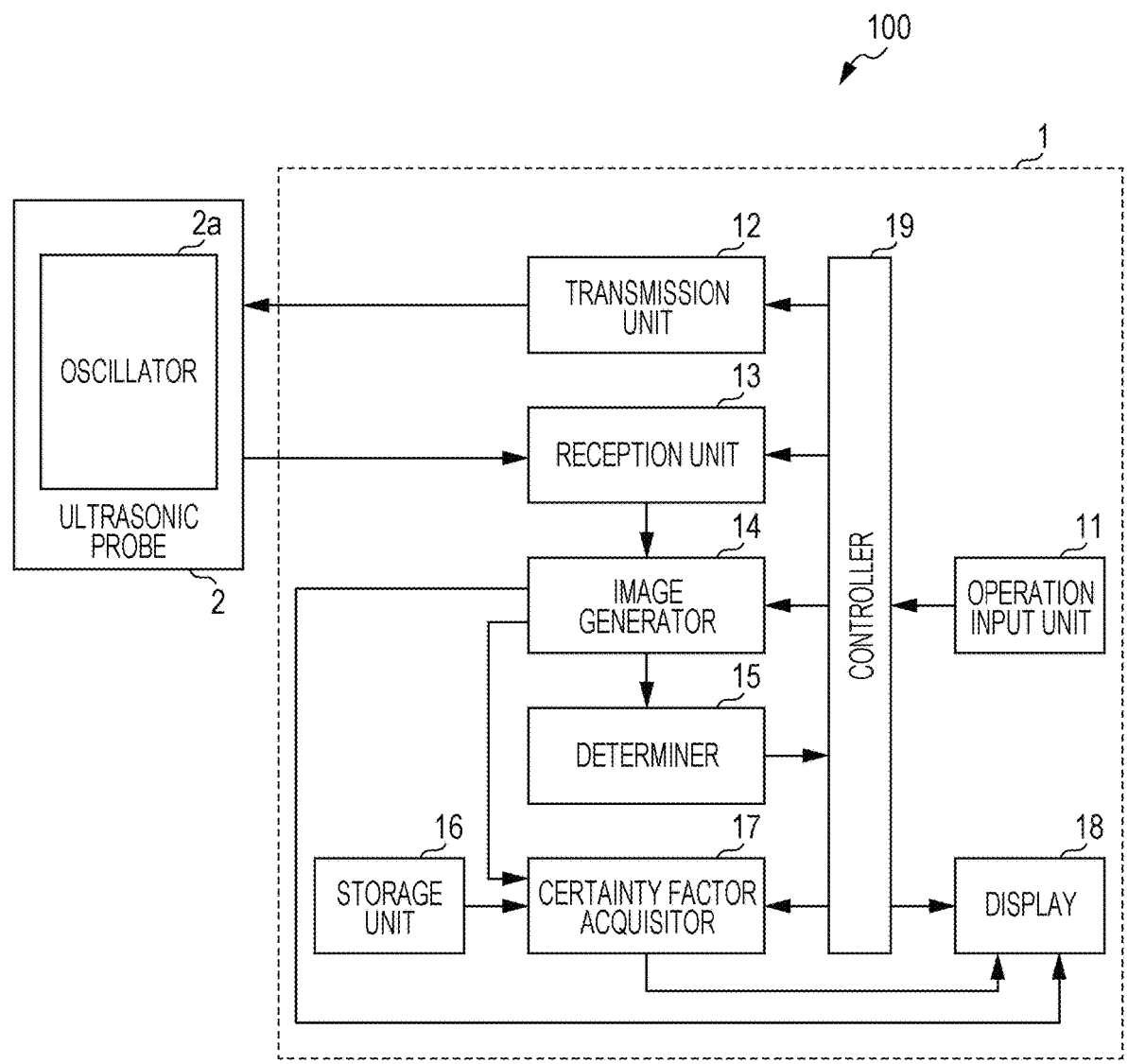
FIG. 2 is a block diagram illustrating a functional configuration of the ultrasonic image diagnostic apparatus.

Next, a functional configuration of the ultrasonic image diagnostic apparatus 100 will be described with reference to FIG. 2. FIG. 2 is a block diagram illustrating a functional configuration of the ultrasonic image diagnostic apparatus 100.

As illustrated in FIG. 2, the ultrasonic image diagnostic apparatus main body 1 includes an operation input unit 11, a transmission unit 12, a reception unit 13, an image generator 14, a determiner 15, a storage unit 16, a certainty factor acquisitor 17, a display 18, and a controller 19. Note that the certainty factor acquisitor 17 functions as an "ultrasonic image acquisitor" and an "identification result acquisitor" of the present invention. The controller 19 functions as an "identifier changer" of the present invention.

The operation input unit 11 includes various switches, buttons, a track pad, a trackball, a mouse, a keyboard, a touch panel that is integrally provided on a display screen of the display 18 and detects a touch operation on the display screen, and the like. The operation input unit 11 performs, for example, attachment and detachment (connection and release) of the ultrasonic probe 2, selection of a diagnosis site (preset), diagnosis start and diagnosis end, selection of a measurement item, activation and termination of a device or an application, freeze start and release, input of a command for instructing selection of a processor that performs identification processing of an identification target object using an identifier, data such as personal information of a subject, and various parameters for displaying an ultrasonic image on the display 18. Examples of the processor that performs identification processing of an identification target object using the identifier include a central processing unit (CPU), a graphics processing unit (GPU), a field programmable gate array (FPGA), and the like. The operation input unit 11 outputs an operation signal corresponding to an input operation to the controller 19.

Note that measurement items to be selected via the operation input unit 11 are morphological measurements (for example, length, area, angle, velocity, and volume) using an ultrasonic image, measurements (for example, a histogram) using a luminance value, cardiac measurements, gynecological measurements, obstetric measurements, and the like.

The transmission unit 12 is a circuit that supplies a drive signal, which is an electric signal, to the ultrasonic probe 2 via the cable 3 and causes the ultrasonic probe 2 to generate the transmission ultrasonic waves under control of the controller 19.

Further, the transmission unit 12 includes, for example, a dock generation circuit, a delay circuit, and a pulse generation circuit. The clock generation circuit is a circuit that generates a clock signal that determines a transmission timing and a transmission frequency of the drive signal. The delay circuit is a circuit for setting a delay time for each individual path corresponding to each oscillator 2a, and delaying transmission of the drive signal by the set delay time for focusing a transmission beam including the transmission ultrasonic waves (transmission beam forming), and the like. The pulse generation circuit is a circuit for generating a pulse signal as the drive signal at a set voltage and a time interval.

The transmission unit 12 configured as described above sequentially switches the plurality of oscillators 2a that supplies the drive signal while shifting a predetermined number for each transmission and reception of ultrasonic waves under control of the controller 19, and supplies the drive signal to the plurality of oscillators 2a to which output is selected, thereby performing scanning.

The reception unit 13 is a circuit that receives a reception signal, which is an electric signal, from the ultrasonic probe 2 via the cable 3 under control of the controller 19. The reception unit 13 includes, for example, an amplifier, an A/D conversion circuit, and a phasing addition circuit.

The amplifier is a circuit for amplifying a reception signal at a preset amplification factor for each individual path corresponding to each oscillator 2a. The A/D conversion circuit is a circuit for analog-to-digital conversion (A/D conversion) of the amplified reception signal. The phasing addition circuit adjusts a time phase by giving a delay time for each individual path corresponding to each oscillator 2a to the A/D-converted reception signal, and adds (phasing addition) these reception signals to generate sound line data. That is, the phasing addition circuit performs reception beam forming on the reception signal for each oscillator 2a to generate sound line data.

The image generator 14 performs envelope detection processing, logarithmic compression, and the like on the sound line data from the reception unit 13 under control of the controller 19, adjusts the dynamic range and gain, and performs brightness conversion, thereby generating B mode image data (hereinafter, ultrasonic image data) as two-dimensional tomographic image data. That is, the ultrasonic image data represents intensity of the reception signal by luminance. The image generator 14 outputs the generated ultrasonic image data to the determiner 15, the certainty factor acquisitor 17, and the controller 19. Note that the image generator 14 may generate A-mode image data, M-mode image data (two-dimensional tomographic image data), Doppler image data, color mode image data, or three-dimensional image data.

Further, the image generator 14 includes an image memory unit (not illustrated) including a semiconductor memory such as a dynamic random access memory (DRAM). The image generator 14 causes the generated ultrasonic image data to be stored in the image memory unit in frame units.

Further, the image generator 14 performs image processing such as image filtering processing and time smoothing processing on the ultrasonic image data read from the image memory unit, and scan-converts the ultrasonic image data into a display image pattern for display on the display 18.

The determiner 15 analyzes the ultrasonic image data output from the image generator 14 and determines an image pattern of an ultrasonic image corresponding to the ultrasonic image data. Specifically, the determiner 15 determines a body site captured in the ultrasonic image, or determines a state that the ultrasonic probe 2 is not in contact with the body (aerial radiation state). Then, the determiner 15 outputs determination result information indicating a determination result of the ultrasonic image to the controller 19. The determination result information includes body site information indicating a limb, a neck, a waist, and the like, anatomical information indicating a nerve (median nerve, ulnar nerve, radial nerve, and brachial plexus), a muscle, a blood vessel, and the like, and information indicating whether or not it is an aerial radiation state.

The storage unit 16 is a storage unit capable of writing and reading information, such as a flash memory, a hard disk drive (HDD), or a solid state drive (SSD).

In the present embodiment, the storage unit 16 stores a plurality of identifiers (convolutional neural networks: CNNs) used by the certainty factor acquisitor 17 to identify an identification target object captured in an ultrasonic image generated by the image generator 14.

Here, the identification target object is a nerve, a fascia, a muscle, a blood vessel, a needle, a heart, a placenta, a lymph node, a brain, a prostate, a carotid artery, or a breast, and may be an organ itself or a body structure such as a limb, a face, a neck, or a waist without being limited to a detailed structure, or may be a lesion part indicating some disease or an abnormal luminance region in the ultrasonic image. The storage unit 16 stores a plurality of identifiers optimized to increase the identification accuracy of the identification target object for each identification target object.

The convolutional neural network is a type of forward propagation neural network, and is based on knowledge in the structure of the visual field of the brain. Basically, the convolutional neural network has a structure in which a convolution layer responsible for local characteristic extraction of an image and a pooling layer (sub-sampling layer) that collects characteristics locally are repeated. By respective layers of the convolutional neural network, a plurality of neurons is possessed, and individual neurons are arranged in a form corresponding to the visual field. The basic function of each neuron includes input and output of a signal. However, when a signal is transmitted between neurons of each layer, the input signal is not output as it is and a connection load is set for each input, and when the sum of weighted inputs exceeds a threshold set for each neuron, a signal is output to the neuron of the next layer. The connection load between these neurons is calculated from the teaming data. Accordingly, the output value can be estimated by inputting real-time data. Examples of known convolutional neural network models include GoogleNet, ResNet, SENet, U-Net, MobileNet, and the like, but an algorithm constituting the convolutional neural network is not particularly limited as long as the convolutional neural network is suitable for this purpose.

The identifier has pre-learned so as to input the ultrasonic image data generated by the image generator 14 and output, for each predetermined portion constituting the ultrasonic image, a certainty factor representing a probability that the identification target object (specifically, a position, a boundary, or a region of the identification target object) is captured in the ultrasonic image corresponding to the ultrasonic image data. In the present embodiment, the certainty factor output from the identifier is represented by a value larger than zero and equal to or less than one. That means that the higher the certainty factor, the higher the probability that the identification target object is captured on the ultrasonic image.

The learning process on the identifier is performed by known supervised learning, specifically, adjustment of network parameters including a weighting factor, a bias, and the like using error back propagation method (backpropagation) on the basis of teacher data prepared in advance. The teacher data is a set of ultrasonic image data generated in the past and correct answer data corresponding thereto. As the correct answer data, for example, a labeling image obtained by labeling a desired region in the ultrasonic image corresponding to the ultrasonic image data with an arbitrary value, coordinate data indicating the desired region by coordinates, a linear or curved equation indicating a boundary of the desired region, or the like is used. In the present embodiment, the labeling image is used as the correct answer data, and in the ultrasonic image as the teacher data, "1" is labeled in a portion in which the identification target object is captured, and "0" is labeled in a portion in which the identification target object is not captured.

Note that the identifier is not limited to the convolutional neural network, and a mathematical model including a calculation algorithm and a coefficient may be used. Further, the storage unit 16 may include an identifier (general-purpose model, corresponding to "first identifier" of the present invention) that has learned to output a certainty factor representing a probability that a plurality of identification target objects (corresponding to a plurality of general-purpose sites (classes)) is captured on the input ultrasonic image, and an identifier (dedicated model, corresponding to "second identifier" of the present invention) that has learned to output a certainty factor representing a probability that a specific identification target object (corresponding to a specific site) is captured on the input ultrasonic image. Furthermore, the storage unit 16 may store, as identifiers used by the certainty factor acquisitor 17 to identify the same identification target object, an identifier of a responsivity prioritized model that emphasizes responsiveness (identification processing time, real-time property) rather than identification accuracy, and an identifier of an identification accuracy prioritized model that emphasizes identification accuracy rather than responsiveness.

The certainty factor acquisitor 17 reads the identifier specified by identifier identification information output from the controller 19 from the storage unit 16, and inputs the ultrasonic image data generated by the image generator 14 to the identifier. Then, the certainty factor acquisitor 17 acquires the certainty factor output from the identifier for each predetermined region constituting the ultrasonic image corresponding to the ultrasonic image data, and outputs the certainty factor information indicating the acquired certainty factor to the display 18.

The display 18 is a display device such as a liquid crystal display (LCD), a cathode-ray tube (CRT) display, an organic electronic luminescence (EL) display, an inorganic EL display, and a plasma display. The display 18 displays a display image based on the ultrasonic image corresponding to the ultrasonic image data generated by the image generator 14 and the certainty factor information output from the certainty factor acquisitor 17 on the display screen under control of the controller 19.

Figure 3A:
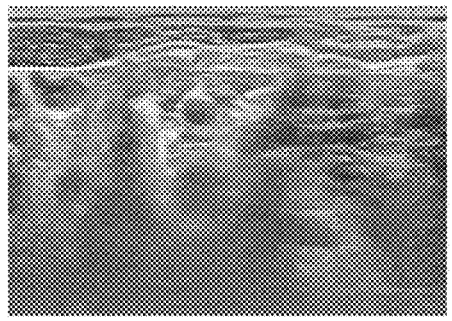
FIG. 3A is a diagram illustrating an example of a display image displayed by a display.
Figure 3B:
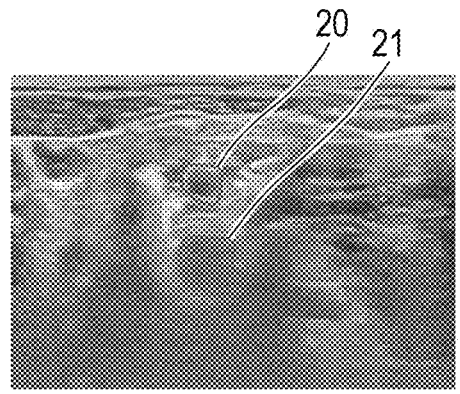
FIG. 3B is a diagram illustrating an example of a display image displayed by the display.

FIGS. 3A to 3E are diagrams illustrating examples of a display image displayed by the display 18. FIG. 3A is a diagram illustrating an example of an ultrasonic image corresponding to the ultrasonic image data as the display image. FIG. 3B is a diagram illustrating an example of a superimposed image in which boundary images 20 and 21 indicating boundaries of identification target objects are superimposed on an ultrasonic image corresponding to ultrasonic image data as a display image. The boundary of the identification target object represented by the boundary images 20 and 21 includes a portion where the certainty factor indicated by the certainty factor information output from the certainty factor acquisitor 17 is equal to or more than a predetermined value, that is, a portion having a high probability that the boundary of the identification target object is captured.

Figure 3C:
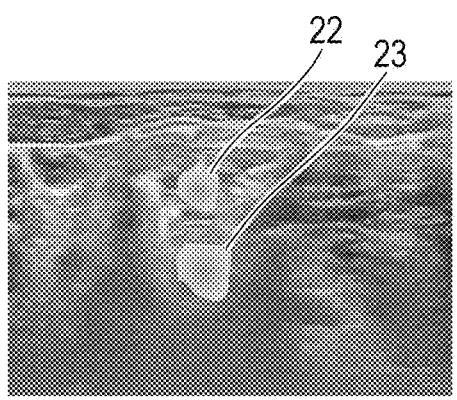
FIG. 3C is a diagram illustrating an example of a display image displayed by the display.

FIG. 3C is a diagram illustrating an example of a superimposed image in which region images 72 and 23 each indicating a region of the identification target object are superimposed on an ultrasonic image corresponding to ultrasonic image data as a display image. The region of the identification target object represented by the region image 22 or 23 includes a portion in which the certainty factor indicated by the certainty factor information output from, the certainty factor acquisitor 17 is equal to or more than a predetermined value, that is, a portion having a high probability that the region of the identification target object is captured.

Figure 3D:
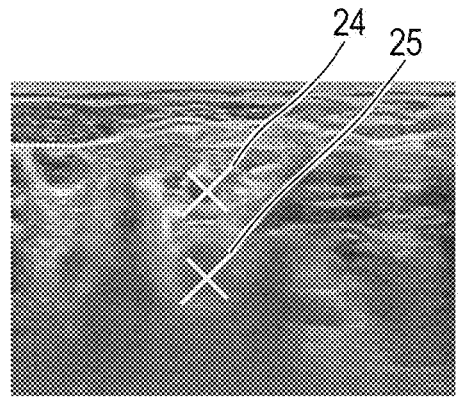
FIG. 3D is a diagram illustrating an example of a display image displayed by the display.
Figure 3E:
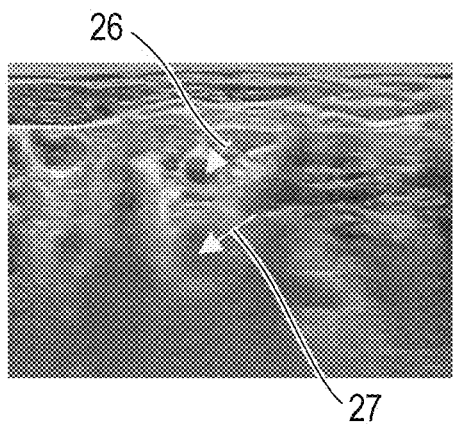
FIG. 3E is a diagram illustrating an example of a display image displayed by the display.

FIG. 3D is a diagram illustrating an example of a superimposed image in which position images 24 and 25 each indicating the position of the identification target object with × mark are superimposed on the ultrasonic image corresponding to the ultrasonic image data as the display image. The position of the identification target object represented by the position image 24 or 25 includes a portion where the certainty factor indicated by the certainty factor information output from the certainty factor acquisitor 17 is equal to or more than a predetermined value, that is, a portion having a high probability that the position of the identification target object is captured. Note that as illustrated in FIG. 3E, a superimposed image in which position images 26 and 27 indicating the positions of the identification target objects by arrows are superimposed on the ultrasonic image corresponding to the ultrasonic image data may be displayed as the display image on the display screen. Further, although not illustrated, a superimposed image in which a position image indicating the position of the identification target object as a point is superimposed on the ultrasonic image corresponding to the ultrasonic image data may be displayed on the display screen as the display image.

By checking the superimposed image in which the identification target object is highlighted on the display screen, the user can intuitively grasp a portion in which the position, boundary, or region of the identification target object is captured in the ultrasonic image. For example, by highlighting the nerve structure such as the peripheral nerve on the display screen, the user can easily grasp a nerve region that is difficult to grasp even by a specialist in a normal ultrasonic image, and thus, for example, can easily perform treatment such as puncture. Alternatively, by highlighting the organ such as the brain of the fetus, the user can easily grasp the growth state of the organ that is difficult to grasp, and thus can easily grasp the presence or absence of a congenital or acquired problem.

The controller 19 includes, for example, a central processing unit (CPU), a read only memory (ROM), and a random access memory (RAM), reads various processing programs such as a system program stored in the ROM, expands the programs in the RAM, and centrally controls operation of each part of the ultrasonic image diagnostic apparatus main body 1 according to the expanded program.

The ROM includes a non-volatile memory or the like of a semiconductor or the like, and stoics a system program corresponding to the ultrasonic image diagnostic apparatus 100, various processing programs that can be executed on the system program, various data such as a gamma table, and the like. These programs are stored in the form of a computer-readable program code, and the CPU sequentially executes operations according to the program code. The RAM forms a work area that temporarily stores various programs executed by the CPU and data related to these programs. In the present embodiment, a "identifier changing program" is stored in the ROM of the controller 19.

The controller 19 selects an identifier to which the ultrasonic image data generated by the image generator 14 is input in the certainty factor acquisitor 17. Then, the controller 19 outputs the identifier identification information for identifying the selected identifier to the certainty factor acquisitor 17. Here, selecting the identifier to which the ultrasonic image data is input includes changing only a part of the identifier or changing the entire identifier. When only a part of the identifier is changed, only the coefficient (parameter) used in the calculation algorithm may be changed without changing the calculation algorithm of the identifier. In a case where only a part of the identifier is changed in this manner, since the speed at which the identifier is switched becomes faster, it is possible to reduce the delay that occurs until the identifier is switched to a new identifier.

For example, the controller 19 changes the identifier to which the ultrasonic image data is input in the certainty factor acquisitor 17 according to an operation input to the operation input unit 11 (operation input by the user to the ultrasonic image diagnostic apparatus 100). For example, when the user does not directly designate the identifier via the operation input unit 11 (for example, in a case where only a diagnosis site is designated, in a case where activation or termination of an application, start or termination of freeze, or the like is instructed), the controller 19 determines the identifier to which the ultrasonic image data is input in the certainty factor acquisitor 17 according to the operation input to the operation input unit 11. For example, in a case where the waist is designated as the diagnosis site, the controller 19 determines the identifier for identifying the sciatic nerve (identification target object) as the identifier to which the ultrasonic image data is input in the certainty factor acquisitor 17. Thus, since the identifier is appropriately changed (switched) by a natural diagnosis workflow (for example, selection of a diagnosis site, preset selection of an inspection condition, and the like) usually performed by the user, it is possible to eliminate time and labor of the user to switch the identifier one by one.

Further, when the user directly designates the identifier via the operation input unit 11, the controller 19 determines the designated identifier as the identifier to which the ultrasonic image data is input in the certainty factor acquisitor 17. In this case, since the superimposed image in which the identification target object identified by the designated identifier is superimposed on the ultrasonic image is displayed on the display screen, the user can intuitively grasp a portion in which the position, boundary, or region of the identification target object is captured in the ultrasonic image.

Note that the controller 19 may also determine an identifier different from the directly designated identifier as the identifier to which the ultrasonic image data is input in the certainty factor acquisitor 17. In this case, since the superimposed image in which the identification target object identified by another identifier is superimposed on the ultrasonic image is displayed on the display screen, that is, the supplementary identification target object identified by the other identifier is also highlighted, the user can more intuitively grasp a portion in which the position, boundary, or legion of the identification target object is captured in the ultrasonic image. Furthermore, the controller 19 may determine an identifier designated in the past (for example, an identifier designated at the time of ending diagnosis or freezing) as the identifier to which the ultrasonic image data is input in the certainty factor acquisitor 17.

Furthermore, the controller 19 changes the identifier to which the ultrasonic image data is input in the certainty factor acquisitor 17 according to the type of the identification target object captured in the ultrasonic image corresponding to the ultrasonic image data generated by the image generator 14. Specifically, the controller 19 refers to the determination result information output from the determiner 15, and changes the identifier to which the ultrasonic image data is input in the certainty factor acquisitor 17 according to the type of the identification target object (for example, a body site) captured in the ultrasonic image. Thus, even in a case where the user unexpectedly changes the diagnosis site, the identifier can be appropriately switched, and thus it is possible to eliminate time and labor of the user to switch the identifier one by one. Moreover, there is no risk of showing the user an inappropriate identification result on the display screen, and erroneous diagnosis by the user can be prevented. Note that the controller 19 may change the identifier to which the ultrasonic image data is input in the certainty factor acquisitor 17 according to the type of the identification target object captured in the ultrasonic image and the operation input to the operation input unit 11.

The controller 19 refers to the determination result information output from, the determiner 15, and changes the identifier to which the ultrasonic image data is input in the certainty factor acquisitor 17 according to the type of the identification target object (for example, a body site) captured in the ultrasonic image at the timing when the state is switched from the aerial radiation state to the state where the ultrasonic probe 2 is in contact with the body. The user sometimes moves the ultrasonic probe 2 away from the body in a case where the user changes the diagnosis site or in a case where the user feels that it is difficult to see a desired body site. In such a case, by appropriately changing the identifier at the timing when the state is switched from the aerial radiation state to the state where the ultrasonic probe 2 is in contact with the body, the user can eliminate time and labor of switching the identifier one by one, and the user can intuitively grasp a portion in which the position, boundary, or region of the identification target object is captured in the ultrasonic image displayed on the display screen in a natural flow.

Note that the controller 19 may refer to the determination result information output from the determiner 15 to start or end the identification processing of the identifier in the certainty factor acquisitor 17 or start or end freezing. Thus, in a case where the user unexpectedly changes the diagnosis site or in a case where the ultrasonic probe 2 is separated from the body, it is possible to prevent the identification processing of the identifier and the display of the ultrasonic image and the like from being performed, and there is no risk of showing the user an inappropriate identification result on the display screen, and erroneous diagnosis by the user can be prevented. Moreover, the power consumption of the ultrasonic image diagnostic apparatus 100 can be saved by preventing the identification processing of the identifier and the display of the ultrasonic image and the like from being unnecessarily performed.

Further, the controller 19 refers to the determination result information output from the determiner 15, and in a case where the aerial radiation state continues for a certain period of time, the previous identification result of the identifier may be reset once and returned to the default (preset) identifier again. In a case where the ultrasonic probe 2 is separated once from the body and the ultrasonic probe 2 is placed onto the body again, the site can be different from the site diagnosed until immediately before. When the location to which the ultrasonic probe 2 is placed is changed, the characteristics of the ultrasonic image greatly change. Thus, by selecting identifiers (general-purpose models) corresponding to various sites, for example, at the stage of being in the aerial radiation state for a certain period of time, the user can quickly grasp an anatomical structure in the ultrasonic image displayed on the display screen without requiring an operation to select an unnecessary identifier.

Further, the controller 19 changes the identifier to which the ultrasonic image data is input in the certainty factor acquisitor 17 according to the type (the linear scanning method, the sector scanning method, the convex scanning method, the radial scanning method, or the circular scanning method) of the ultrasonic probe 2. Since an image size, a frame rate, and image quality that can be visualized are different depending on the difference in the type of the ultrasonic probe 2, by optimizing the identifier according to the type of the ultrasonic probe 2, even if the ultrasonic probe 2 used by the user is changed each time, a stable identification result can be acquired in the certainty factor acquisitor 17.

Further, the controller 19 changes the identifier to which the ultrasonic image data is input in the certainty factor acquisitor 17 according to the identification result (for example, a maximum value, an average value, a most frequent value, a standard deviation, or the like of the certainty factor) of the identifier. For example, the controller 19 changes the identifier to an identifier having a higher certainty factor (higher identification accuracy) according to the identification result of the identifier. Thus, the certainty factor acquisitor 17 can acquire a highly accurate identification result. Further, the controller 19 changes the identifier to the identifier having the most stable certainty factor with respect to time according to the identification result of the identifier. The fact that the certainty factor is stable with respect to time indicates that the identification accuracy is high, and thus it is possible to display a highly accurate identification result (superimposed image) on the display screen. Further, the identification result of which the certainty factor is unstable with respect to time is no longer unnecessarily shown to the user, and it is possible to prevent deterioration of the diagnosis workflow of the user.

Further, the controller 19 changes the identifier to which the ultrasonic image data is input in the certainty factor acquisitor 17 according to the processing time related to the identification of the identifier. Here, the processing time related to the identification of the identifier is a processing time from start to end of the identification processing of the identifier, or a time (including a communication delay time) from start to end of the identification processing of the identifier and until the identification result is superimposed and displayed on the ultrasonic image. For example, the controller 19 changes the identifier to an identifier with higher responsiveness (real-time property)) according to the processing time related to identification of the identifier. Thus, responsiveness related to identification of the identifier is improved without deteriorating identification accuracy of the identifier so that the diagnosis workflow of the user is improved, and a quick treatment of the user can be performed.

As described above in detail, in the present embodiment, the ultrasonic image diagnostic apparatus 100 includes an ultrasonic image acquisitor (certainty factor acquisitor 17) that acquires an ultrasonic image generated on the basis of a reception signal obtained by an ultrasonic probe 2 that transmits and receives ultrasonic waves to and from a subject, an identification result acquisitor (certainty factor acquisitor 17) that acquires, by inputting the ultrasonic image acquired to any of a plurality of identifiers that identifies an identification target object captured in an input ultrasonic image, an identification result output from the identifier, and an identifier changer (controller 19) that changes the identifier to which the ultrasonic image acquired is input.

According to the present embodiment configured as described above, for example, the identifier to which the ultrasonic image is input is changed and optimized according to the body site of interest of the user, the measurement target, the processor that performs the identification processing, the type of the ultrasonic probe 2, and the like, and thus it is possible to achieve both the identification accuracy of the identification target object captured in the ultrasonic image and the real-time property of the display (the result of the image processing is displayed as soon as possible). Further, since the identifier is appropriately switched in the natural diagnosis workflow (for example, selection of a diagnosis site, preset selection of an inspection condition, start or release of freezing, and the like) usually performed by the user, the user does not need time and labor to switch the identifier one by one, and can concentrate on a treatment that the user originally desires to perform. Furthermore, the user does not need to search for which identifier is optimal, the real-time property of display is improved, and unnecessary processing in the ultrasonic image diagnostic apparatus 100 can be reduced. Moreover, this makes it possible to improve the responsiveness and accuracy of the separate processing (for example, color Doppler processing, needle point emphasis processing, and the like) performed in parallel.

Note that, in the above embodiment, when the identifier to which the ultrasonic image data is input is not appropriate in the certainty factor acquisitor 17, or when the identification processing of the identifier is not completed by the requested timing (that is, it is not in time), the image indicating the identification target object may not be superimposed on the ultrasonic image corresponding to the ultrasonic image data, and a superimposed image in which the image indicating the identification target object is superimposed on the ultrasonic image may be displayed at an appropriate timing of the next or subsequent frame. Thus, since unnecessary information does not need to be shown to the user, it is possible to prevent deterioration of the diagnosis workflow of the user.

Furthermore, in the above embodiment, when a superimposed image in which an image indicating the boundary, the region, and the position of the identification target object is superimposed on the ultrasonic image corresponding to the ultrasonic image data is displayed as the display image on the display screen, the type (for example, ○○ nerve) of the identification target object specified by the determination result of the determiner 15 may also be displayed together.

Further, in the above embodiment, the certainty factor acquisitor 17 may be provided not on the ultrasonic image diagnostic apparatus 100 but on another server (another computer). In this case, the ultrasonic image diagnostic apparatus 100 and the other server correspond to the "ultrasonic image diagnostic apparatus" of the present invention. There is a case where the processor on the ultrasonic image diagnostic apparatus 100 does not have sufficiently high processing performance (particularly in a case of an old model), and when identification processing is performed by a certain identifier, there is a case where a request of the user is not satisfied from the viewpoint of processing speed or identification accuracy. Accordingly, the certainty factor acquisitor 17 provided on the other server (a computer having a processor with a higher specification) receives the ultrasonic image data and the identifier selected by the controller 19, performs identification processing using the selected identifier, transmits the identification result to the ultrasonic image diagnostic apparatus 100, and causes the identification result to be displayed on the display 18, to thereby enable display of a more accurate identification result at a higher speed.

In the above embodiment, the controller 19 may change the identifier to which the ultrasonic image data is input in the certainty factor acquisitor 17 according to the communication method (wired communication or wireless communication) between the ultrasonic image diagnostic apparatus main body 1 and the ultrasonic probe 2. Since there is a difference in the communication speed due to a difference in the communication system between the ultrasonic image diagnostic apparatus main body 1 and the ultrasonic probe 2, it is possible to achieve both the identification accuracy of the identification target object captured in the ultrasonic image and the real-time property of display by changing the identifier according to the communication system.

Further, in the above embodiment, the controller 19 may change the identifier to which the ultrasonic image data is input in the certainty factor acquisitor 17 according to the inclination or angle of the ultrasonic probe 2. Since the ultrasonic image changes depending on the angle at which the ultrasonic Probe 2 is in contact with the body, by optimizing the identifier to be used in accordance with the angle of the ultrasonic probe 2, it is possible to acquire stable identification results of the identifier with respect to various manners of placing the ultrasonic probe 2.

Further, in the above embodiment, the controller 19 may change the identifier to which the ultrasonic image data is input in the certainty factor acquisitor 17 according to the information of the subject (for example, the name, age, sex, body mass index (BMI), history of injury or illness, and the like of a patient). Since the physical characteristics are different depending on the age, sex, BMI and medical history of the patient who is the subject, the characteristics of the ultrasonic image are changed. Therefore, by changing the identifier according to the information of the subject, it is possible to achieve both the identification accuracy of the identification target object captured in the ultrasonic image and the real-time property of display even for subjects having different physical characteristics.

Further, in the above embodiment, the controller 19 may change the identifier to which the ultrasonic image data is input in the certainty factor acquisitor 17 according to the information of the user using the ultrasonic image diagnostic apparatus 100 (for example, which doctor or technician is currently using the apparatus, or the like). Since the manner of placing the ultrasonic probe 2 differs depending on the user, the ultrasonic image changes depending on the user. Therefore, by changing the identifier according to the information of the user who uses the ultrasonic image diagnostic apparatus 100, the identification accuracy of the identification target object captured in the ultrasonic image and the real-time property of display can be optimized for each user.

Further, in the above embodiment, the controller 19 may first select an identifier for identifying a thick nerve (identification target object), grasp an outline of the identification target object, and change the identifier to an identifier for identifying a fine nerve (identification target object) when a cross section desired to be viewed to some extent is determined. Thus, the user can check the superimposed image in which the image indicating the identification target object is superimposed on the ultrasonic image on the display screen, and can grasp a thin nerve with more security by tracing to a region that becomes thinner from a thick nerve rather than suddenly searching for the fine nerve.

In addition, in the above embodiment, the controller 19 may first select an identifier (general-purpose model) corresponding to a plurality of general-purpose sites (classes), perform scanning (scanning) for a while, and then select an identifier (dedicated model) specialized for a specific site (class). In this case, the display 18 may display an identifier (dedicated model) as a selection candidate on the display screen so as to be selectable by the user. In a case where the manner of placing the ultrasonic probe 2 is not appropriate, or the like, since a desired site cannot be drawn as an image in the first place, even a dedicated model (identifier) specialized for a certain site cannot be accurately identified, and use of the dedicated model from the early stage may be inappropriate. In particular, in a case of a beginner, displaying more information such as identification results of multiple sites, although having slightly poorer accuracy, may be more appropriate than displaying information of a limited site by a dedicated model for the reasons that anatomical understanding is facilitated, and that an approximate position of a region desired by the user, that is, the position of the ultrasonic probe 2 to be placed can be quickly grasped, and the like. Thus, at the start of placement of the ultrasonic probe 2, the identification results are displayed for a plurality of sites, and the model is switched to the dedicated model at the stage when the cross section is fixed, that is, when the identification target object to be identified is narrowed, so that the user can smoothly grasp a desired site (identification target object).

Further, in the above embodiment, with respect to the transmission unit 12, the reception unit 113, the image generator 14, the determiner 15, the certainty factor acquisitor 17, and the controller 19 included in the ultrasonic image diagnostic apparatus 100, a part or all of the functions of respective functional blocks can be achieved as a hardware circuit such as an integrated circuit. The integrated circuit is, for example, a large scale integrated circuit (LSI), and the LSI may also be called an integrated circuit (IC), a system LSI, a super LSI, or an ultra LSI depending on the degree of integration. In addition, the circuit integration method is not limited to the LSI and may be achieved by a dedicated circuit or a general-purpose processor, or a reconfigurable processor capable of reconfiguring connection and setting of circuit cells inside the FPGA or the LSI may be used. Further, a part or all of the functions of each functional block may be executed by software. In this case, this software is stored in one or more storage media such as ROM, an optical disk, a hard disk, or the like, and this software is executed by an arithmetic processor.

Although embodiments of the present invention have been described and illustrated in detail, the disclosed embodiments are made for purposes of illustration and example only and not limitation. That is, the present invention can be implemented in various forms without departing from, the gist or the main features thereof. The scope of the present invention should be interpreted by terms of the appended claims.

What is claimed is:

1. An ultrasonic image diagnostic apparatus comprising:
an ultrasonic image acquisitor that acquires an ultrasonic image generated on the basis of a reception signal obtained by an ultrasonic probe that transmits and receives ultrasonic waves to and from a subject;
an identification result acquisitor that acquires, by inputting the ultrasonic image acquired to any of a plurality of identifiers that identifies an identification target object captured in an input ultrasonic image, an identification result output from one of the plurality of identifiers; and
a hardware processor that changes the one of the plurality of identifiers to which the ultrasonic image acquired is input according to a type of the ultrasonic probe.

2. The ultrasonic image diagnostic apparatus according to claim 1, wherein
the hardware processor is configured to change the one of the plurality of identifiers to which the ultrasonic image acquired is input further according to an operation input of a user to the ultrasonic image diagnostic apparatus.

3. The ultrasonic image diagnostic apparatus according to claim 1, wherein
the hardware processor is configured to change the one of the plurality of identifiers to which the ultrasonic image is input further according to a type of the identification target object captured in the ultrasonic image acquired.

4. The ultrasonic image diagnostic apparatus according to claim 3, further comprising
a determiner that determines the type of the identification target object captured in the ultrasonic image acquired.

5. The ultrasonic image diagnostic apparatus according to claim 1, wherein
the hardware processor is configured to change the one of the plurality of identifiers to which the ultrasonic image acquired is input further according to an identification result of the identifier.

6. The ultrasonic image diagnostic apparatus according to claim 1, wherein
the hardware processor is configured to change the one of the plurality of identifiers to which the ultrasonic image acquired is input further according to a processing time related to identification of the identifier.

7. The ultrasonic image diagnostic apparatus according to claim 1, wherein the one of the plurality of identifiers is configured to lean to output a certainty factor representing a probability that an identification target object is captured in an input ultrasonic image.

8. The ultrasonic image diagnostic apparatus according to claim 7, wherein
the plurality of identifiers includes:
a first identifier that has learned to output a certainty factor representing a probability that a plurality of identification target objects is captured on the input ultrasonic image; and
a second identifier that has learned to output a certainty factor representing a probability that a specific identification target object is captured on the input ultrasonic image.

9. The ultrasonic image diagnostic apparatus according to claim 1, further comprising
a display that displays a display image based on the ultrasonic image acquired and the identification result.

10. An identifier changing method comprising:
acquiring an ultrasonic image generated on the basis of a reception signal obtained by an ultrasonic probe that transmits and receives ultrasonic waves to and from a subject;
acquiring, by inputting the ultrasonic image acquired to any of a plurality of identifiers that identifies an identification target object captured in an input ultrasonic image, an identification result output from one of the plurality of identifiers; and
changing the one of the plurality of identifiers to which the ultrasonic image acquired is input according to a type of the ultrasonic probe.

11. A non-transitory recording medium storing a computer readable identifier changing program causing
a computer to perform:
acquiring an ultrasonic image generated on the basis of a reception signal obtained by an ultrasonic probe that transmits and receives ultrasonic waves to and from a subject;
acquiring, by inputting the ultrasonic image acquired to any of a plurality of identifiers that identifies an identification target object captured in an input ultrasonic image, an identification result output from one of the plurality of identifiers; and
changing the one of the plurality of identifiers to which the ultrasonic image acquired is input according to a type of the ultrasonic probe.

12. The ultrasonic image diagnostic apparatus according to claim 1, wherein
the hardware processor is configured to change the one of the plurality of identifiers to which the ultrasonic image acquired is input at a timing when a state is switched from an aerial radiation state to a state where the ultrasonic probe is in contact with the subject.

13. The ultrasonic image diagnostic apparatus according to claim 1, further comprises an ultrasonic image diagnostic apparatus main body connected to the ultrasonic probe via wired communication or wireless communication, the ultrasonic image diagnostic apparatus main body including the ultrasonic image acquisitor, the identification result acquisitor and the hardware processor, wherein
the hardware processor is configured to change the one of the plurality of identifiers to which the ultrasonic image acquired is input further according to a communication method between the ultrasonic image diagnostic apparatus main body and the ultrasonic probe.

14. The ultrasonic image diagnostic apparatus according to claim 1, wherein
the hardware processor is configured to change the one of the plurality of identifiers to which the ultrasonic image acquired is input further according to an angle at which the ultrasonic probe is in contact with the subject.

15. The ultrasonic image diagnostic apparatus according to claim 1, wherein
the hardware processor is configured to change the one of the plurality of identifiers to which the ultrasonic image acquired is input further according to information of the subject including at least one selected from a group consisting of a name, an age, a sex, a body mass index, a history of injury and a history of illness.

16. The ultrasonic image diagnostic apparatus according to claim 1, wherein
the hardware processor is configured to change the one of the plurality of identifiers to which the ultrasonic image acquired is input further according to information of a user using the ultrasonic image diagnostic apparatus.

* * * * *